(12) United States Patent
Deuel (10) Patent No.: US 6,596,323 B1
(45) Date of Patent: Jul. 22, 2003

(54) MEADOWFOAM PLANT MATERIAL HAVING EXOGENOUS PLANT GROWTH SUBSTANCE AND METHOD OF USE

(75) Inventor: Wes A. Deuel, Beaverton, OR (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 0 days.

(21) Appl. No.: 10/080,987

(22) Filed: Feb. 22, 2002

Related U.S. Application Data (63) Continuation-in-part of application No. 09/597,651, filed on Jun. 20, 2000.
(60) Provisional application No. 60/143,334, filed on Jun. 24, 1999.

(51) Int. Cl.[7] ................................................. A01N 65/00
(52) U.S. Cl. ........................ 424/725; 47/58.1; 435/430; 504/118
(58) Field of Search .......................... 424/725; 47/58.1; 435/430; 504/118

(56) References Cited

U.S. PATENT DOCUMENTS

| | | |
|---|---|---|
| 4,925,581 A | 5/1990 | Erickson et al. |
| 5,023,312 A | 6/1991 | Erickson et al. |
| 5,030,268 A | 7/1991 | Christians |
| 5,291,685 A | 3/1994 | Romaine et al. |

OTHER PUBLICATIONS

Svenson et al. "Field evaluations of meadowform seedmeal to control clubroot . . . " Hortscience vol. 35(3). pp392. Jun. 2000.*

Deuel et al. "Control of clubroot . . . using meadowfoam seedmeal . . . " Hortscience vol. 34(3). pp473. Jun. 1999.*

Vaugh et al, Isolation and Identification of (3–Methoxyphenyl) Acetonitrile as a Phytotoxin From Meadowfoam Seedmen. Journal of Chemical Ecology, vol. 22, Nov. 10, 1996, pp. 1939–1949.

* cited by examiner

Primary Examiner—Leon B. Lankford, Jr.
(74) Attorney, Agent, or Firm—Steven J. Adamson

(57) ABSTRACT

Meadowfoam seedmeal used for plant growth enhancement. Experiments with meadowfoam seedmeal, genus Limnanthes, indicated significant growth enhancement when combined with a growing medium at certain rates. Nutrient exclusion experiments suggested that enhanced growth was not from nutrient supplementation, but hormone induced growth exogenously mediated by the seedmeal. Various target plants and application rates and methods are discussed as are various fertilizer application rates.

19 Claims, 6 Drawing Sheets

MEADOWFOAM PLANT MATERIAL HAVING EXOGENOUS PLANT GROWTH SUBSTANCE AND METHOD OF USE

CROSS-REFERENCE TO RELATED APPLICATIONS

This application is a continuation in part of co-pending U.S. patent application Ser. No. 09/597,651, filed Jun. 20, 2000, having the same inventors as above and entitled Meadowfoam Plant Material as a Plant Growth Regulator. Application No. 09/597,651 claims the benefit of U.S. Provisional Application No. 60/143,334, filed Jun. 24, 1999, having the same inventors and title as Application No. 09/597,651. These earlier filed applications are hereby incorporated by reference.

FIELD OF THE INVENTION

The present invention relates to the use of seedmeal from meadowfoam, genus Limnanthes, or like plants to exogenously achieve plant growth enhancement. The present invention also relates to application rates, with and without fertilizer, to achieve this enhanced growth.

BACKGROUND AND SUMMARY OF THE INVENTION

Plant growth enhancement is a major industry and a paramount concern of agricultural food producers, ornamental stock producers and many residential and commercial landowners. Fertilizer manufacture and distribution is a principal component of the plant growth industry. While fertilizer may take many forms including waste material and manure, commercial fertilizer often consists of nitrogen, phosphorous and potassium (typically abbreviated NPK). In addition to other cellular destinations, nitrogen and phosphorous are needed to construct a cell's DNA, a copy of which is required for each cell division. Nitrogen and phosphorous are typically absorbed through the roots in elemental form or in combination with other atoms, e.g., as small subsets of larger compounds. The availability and uptake of NPK and to a lesser extent other molecules may substantially affect plant growth and yield.

Plant growth is also affected by the presence of plant growth substances, often referred to as "hormones," that are produced in plant tissue and at low concentrations promote, inhibit or qualitatively affect plant growth. Note that these substances are not energy sources or nutrients. Plant growth hormones may generally be grouped into five recognized categories. These are: ethylene and like molecules that promote ripening; abscisic acids that are involved in dormancy and abscission; auxins that stimulate cell extension (typically in actively growing regions); gibberellins that are involved in shoot extension in light; and cytokinins that are often found in roots and involved in cell division and interact with auxin to determine whether dividing cells become root or shoot cells.

The effect of exogenous plant hormones-on recipient plant growth and on fertilizer uptake is not well known, and there is very; limited documentation of successful exogenous plant hormone facilitated plant growth (see reference below). Procurement and application of plant hormones may also be difficult. For these reasons, amongst, others, plant growers typically rely on the application of large amounts of fertilizer as the primary, if not exclusive, way of enhancing plant growth, and not application of plant hormone like substances.

Conventional fertilizer application techniques make large amounts of NPK and similar substances available to plants. These techniques are disadvantageous, however, in that significant quantities of the applied fertilizer are not absorbed by the plant but are blown or washed off into neighboring waterways, often resulting in algae blooms and some degree of putrification of those water resources. A need thus exists to provide plant growth enhancement in a way that replaces conventional fertilizing processes or enhances those processes such that less fertilizer is required and/or that which is applied is more likely to be absorbed by the plant.

Other prior art efforts to increase plant growth include agricultural biotechnology techniques. Agricultural biotechnology may manifest itself in many ways including modification of genes related to: nutrient uptake, de novo synthesis of nutrients; cell elongation; disease resistance; and/or flowering; etc. While agricultural biotechnology holds promise, it is viewed with great suspicion by society due to potential malevolent environmental ramifications. Agricultural biotechnology techniques for plant growth enhancement are also disadvantageous in that they are extremely expensive, long in development and uncertain in their useful lives. A need thus exists to provide plant growth enhancement that does not rely primarily on agricultural biotechnology or "molecular engineering" techniques.

In general, seeds accumulate and store a number of compounds including fatty acids, proteins, sugars, hormones, phenolic acids, tannins and mineral nutrients. Often the hormones or related growth enhancing substances are configured in such a manner or provided in concentrations that render them effective only for the same type of plant. This may to some extent seem intuitive in that in being efficacious to only the same type of plant, they do not facilitate growth of a different type of plant that might compete with their "child" plant. Studies using seedmeal from mustard seed and rape seed plants found limited or no growth enhancement (Oleszek et at., 1994; Johansson and Ascard, 1994, for mustard and Waddington, 1978, for rape seed). Growth stimulus in plant species other than Limnanthes has been attributed to supplemental mineral nutrients present in their seedmeal. There is no evidence from prior studies using seedmeals that shows significant growth enhancement similar to that discussed herein. Experiments using synthetic auxins, cytokinins and/or oligosaccharins have, however, shown that these compound may be involved in limited cell elongation in in vitro grown pea and oat coleoptiles when applied exogenously (Katekar, 1999; Fry, 1999).

To overcome the limitations of prior art plant growth enhancement techniques (often fertilizer based) and to favorably contribute to the critical challenge of increasing plant growth and production, the present invention includes recognition of the exceedingly beneficial effect of meadowfoam seedmeal (MSM) on plant growth and the use of suitable MSM and like substances in this capacity. The present invention includes the use of MSM and like substances in appropriate concentrations, with and without fertilizer, and in various growing media arrangements (e.g., top-dressed, mixed, etc.) to promote plant growth. The beneficial growth attributed to certain concentrations of MSM is apparently achieved, at least in part, by the presence of widely applicable and exceedingly efficacious exogenous hormone like substances (HLS) from MSM. In a top-dressed or mixed media arrangement the growing medium is approximately 7% or less MSM and more desirably from approximately 2–5% MSM. Concentrations above approximately 7.5% by volume tend to have less growth enhancement (in most but not all plants) than concentrations of 2–5% and may even have deleterious effects on plant growth including agravatrophic response.

The present invention includes providing seedmeal that effects plant growth in a manner similar to the beneficial results discussed herein. The plant used in the below discussion is meadowfoam, genus Limnanthes, and particularly the variety *Limnanthes alba* Hartweg ex. Benth (Benth). Since the beneficial properties of Benth are conferred by its genome, any plant having a similar genetic composition in the relevant locations can exhibit the beneficial growth characteristics discussed herein and is thus within the present invention.

The present invention also includes methods of combining MSM with planting medium materials, with and without fertilizer and/or other substances, to achieve a planting medium that enhances plant growth. This combining may include mixing, top-dressing or other ways of combining the MSM or like substances other planting medium material.

DETAILED DESCRIPTION

Meadowfoam, Limnanthes alba, is a herbaceous winter-spring annual, grown as a commercial oilseed crop primarily for its unique fatty acids which are used in the manufacture of lubricants, plastics and cosmetics (Kleiman and Princen, 1991; Savonen, 1997). Meadowfoam seedmeal (MSM) is a byproduct of the distillation process used to extract meadowfoam oil from meadowfoam seed. MSM is generally regarded as a problematic waste of this oil extraction process.

In furtherance of the present invention, experiments were conducted at various locations to assess the efficacy of MSM in enhancing plant growth. The experiments were carried out with meadowfoam seedmeal from *Limnanthes alba* Hartweg ex Benth. The experiments indicated that when applied in at certain rates, with or without fertilizer, MSM appreciable enhanced plant growth. The experiments also indicated that higher rates of application could result in more pronounced phytotoxic symptoms.

Experiments were conducted with ornamental plants and vegetables. The ornamental plant experiments are discussed first followed by a description of the vegetable experiments. Species of ornamentals screened included: Acer, Agrapanthus, Artemisia, Buxus, Carex, Cornus, Dianthus, Dicentra, Dryopteris, Euonymus, Forsythia, Ginko, Heuchera, Hosta, Ilex, Juniperus, Nicotiana, Picea, Potentilla, Prunus, Rhododendron, Rosa, Salvia, Tagetes, Taxus, Thuja, Tiarella, Viburnum, Vinca, Yucca, and Zinnia. Treatments included a control, 1.25%, 2.5%, 5% and 7.5% top-dressed and 5%, 10%, 25% and 50% mixed.

Rates of seedmeal application of approximately 5% by volume top-dressed or incorporated (i.e., mixed) resulted in significantly greater plant height and color compared to controls. In a number of deciduous plants, top-dressed seedmeal treatments (5% or less by volume) resulted in greater chlorophyll content, delay of dormancy in the fall, early break from dormancy in the spring followed by a rapid flush of new growth.

Phytotoxicity symptoms (stunted growth, chlorosis, necrotic tissue, death) occurred at higher treatment rates (~25% by volume and above) when mixed into media of Cornus, Euonymous, Ginko, Juniperus, Potentilla, Rhododendron, Taxus, and Thuja. Top-dressing generally resulted in less phytotoxicity symptoms than incorporation.

With respect to vegetable experiments, the types of vegetables screened included broccoli, cabbage, celery, leek, lettuce, pepper, and squash. Treatments included a control, 2%, 7% and 20% incorporation and a 30% by volume top-dressing in 200 count seedling plug trays.

Treatments containing 2% and 7% seedmeal incorporations resulted in significantly greater color and vigor in all plants and particularly pepper, celery, and squash when compared to controls. MSM treatment resulted in significantly greater chlorophyll levels (leaf chlorophyll content, area concentration was determined using a chlorophyll sensitive photometer).

In treatments containing 20% incorporations and 30% top dressings, the results included inhibition of seedling emergence and phytotoxic symptoms (dwarf growth habit, necrotic tissue, poor color, etc.). The highest degree of phytotoxicity was recorded in the 20% incorporation treatments.

An experiment was also conducted to determine the effects of MSM on the seed potato, Russet Burbank. Treatments included control, 2.5% and 5% mixed. The treatments containing 2.5% and 5% MFM (by volume), resulted in plant height and biomass at least two to three times greater than controls.

The above-described experiments, on both ornamental and vegetable plants, demonstrated significantly enhanced plant growth and occasional agravatrophic response which are both indicative of hormonal influence on the recipient plant. This hormonal influence may be a result of exogenously active plant growth, hormones or similar substances (generally referred to herein as "hormone like substances (HLS)"), hormone precursors, exogenously generated compounds that function in the signal transduction pathway that up-regulates the production of plant growth hormones or their precursors in the recipient plant, or another mechanism. To distinguish the potentially hormonal influences of MSM from "fertilizer effect," it is necessary to analyze both plant growth characteristics and nutrient uptake at various application rates of MSM and various application rates of fertilizer. These experiments are generally referred to as nutrient exclusion experiments.

Nutrient Exclusion Experiments

A series of experiments were conducted to compare the growth characteristics of plants grown with various rates of: a) MSM; b) conventional slow-release fertilizer (F) and c) MSM+F. For these experiments, a commercial fertilizer with slow-release characteristics was chosen for the similarity of its N-P-K profile to that of MSM (though the availability of MSM nutrients is expected to be slower and thus less). Table I shows a comparative breakdown of the nutrients from MSM (determined by analysis) and the subject Scotts™ fertilizer. Soil based biotic and abiotic factors that influence soil dynamics and thus plant growth characteristics were reduced by using 100% sterile perlite in place of soil substrate. Yield and growth characteristic experiments were conducted. The yield experiments used pepper, potato and tomato, and the growth characteristic experiment used tomato. The results of these experiments are shown in FIGS. 1–4 respectively.

TABLE 1

Nutrient comparisons of MSM and Scotts fertilizer.

| Nutrient | MSM* Tissue Analysis | SC** G. Analysis |
|---|---|---|
| N % | 5.13 | 5.50 |
| P % | 1.27 | 1.00 |
| K % | 2.18 | 2.00 |
| S % | 1.47 | 2.38 |
| Ca % | 1.56 | n/a |
| Mg % | 0.64 | 0.30 |
| Mn ppm | 50 | 750 |
| Fe ppm | 436 | 2000 |
| Cu ppm | 7 | 125 |
| B ppm | 32 | n/a |
| Zn ppm | 55 | 250 |

* Meadowfoam seedmeal
** Scotts Customblen (22-4-8) × 0.25

EXAMPLE I

Pepper Yield

Pepper plants (*Capsicum annuum* var. '*Jalapeno*') were grown in a two factorial, randomized block design with 7 replications. Treatments included a commercial slow-release fertilizer (Scotts® Customblen 22-4-8 (N-P-K)) factor at four levels (0, 8, 16 and 24 g top-dressed) and a MSM factor at four levels (0, 2.5, 5 and 7.5% v/v, where v/v=volume/volume). Treatments were prepared by thoroughly mixing various rates of MSM (v/v) with wetted perlite (medium soil grade) in a 50 gal. plastic container to insure even adhesion/distribution of MSM particles onto perlite fraction. Black plastic Treepots™ (Stuewe & Sons, Inc., Corvallis, Oreg.) 10 cm width×36 cm depth (2.83 liter vol.) were fitted with fiberglass screening in bottom to prevent media loss through drain holes and filled with treated media. Controls (untreated perlite) were prepared in the same manner.

Media filled pots were treated with various rates of slow-release fertilizer, placed in a polycarbonate-glazed greenhouse (natural photoperiod May–June, Portland, Oreg.), and irrigated twice daily. At 10 days post-media preparation, pepper seedlings were transplanted into treated pots. At 21 days post-planting, potted plants were moved to an open-air propagation area with same irrigation frequencies. Pepper plants were evaluated at three-week intervals for size, number of flowers, number of fruit and weight of marketable yield. The third evaluation of pepper plants included tissue nutrient analysis of new, fully expanded leaves (discussed in more detail below in Examples V–XVI).

Figure 1:
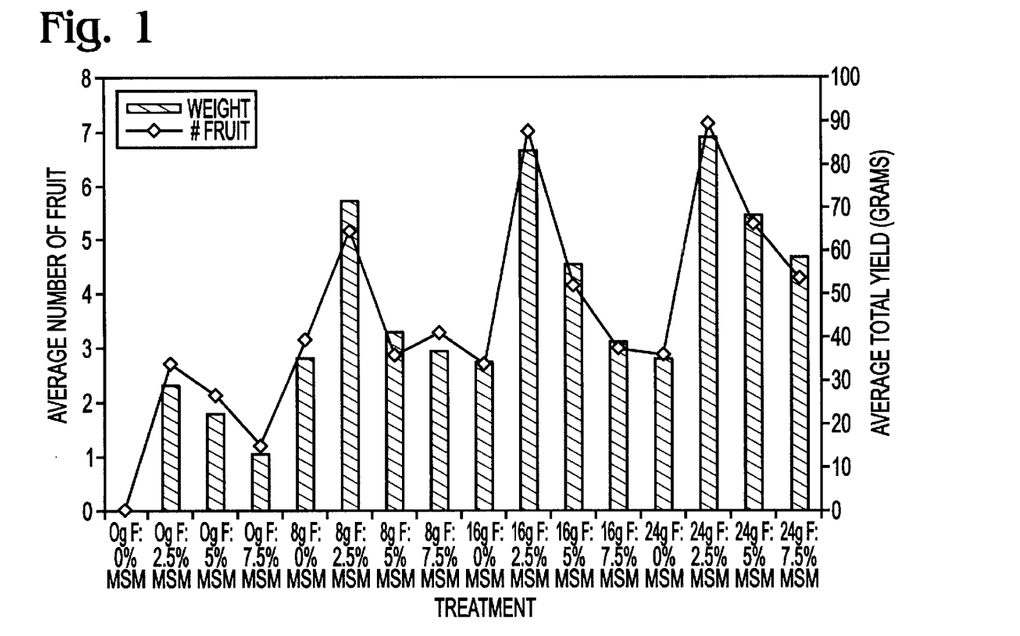
FIGS. 1–3 are diagrams that show yield characteristics for pepper and tomato plants grown with varying MSM and fertilizer rates.
Figure 2:
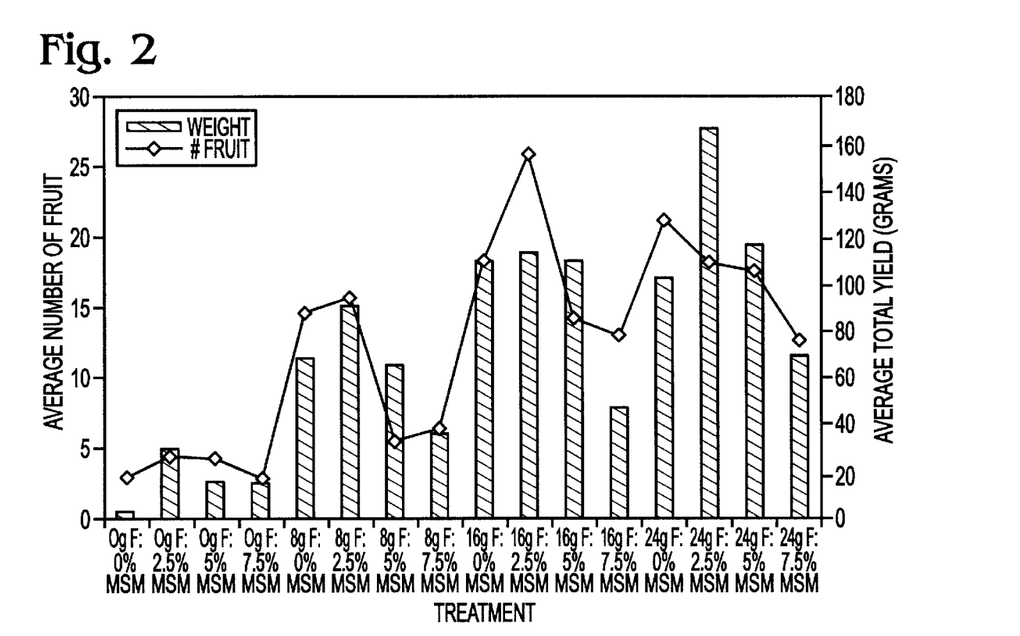
Figure 3:
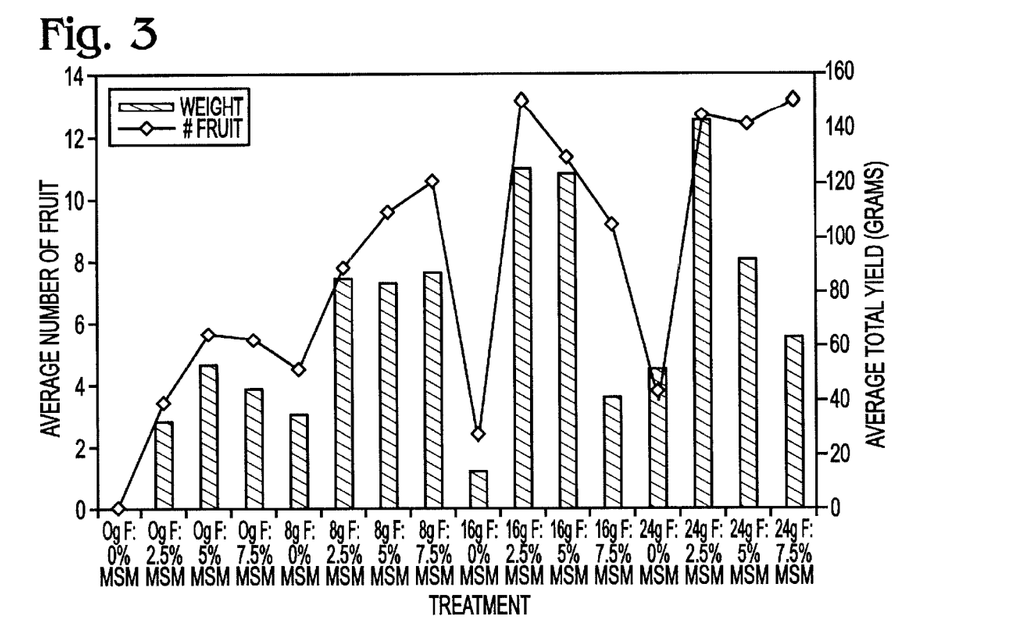
Figure 4:
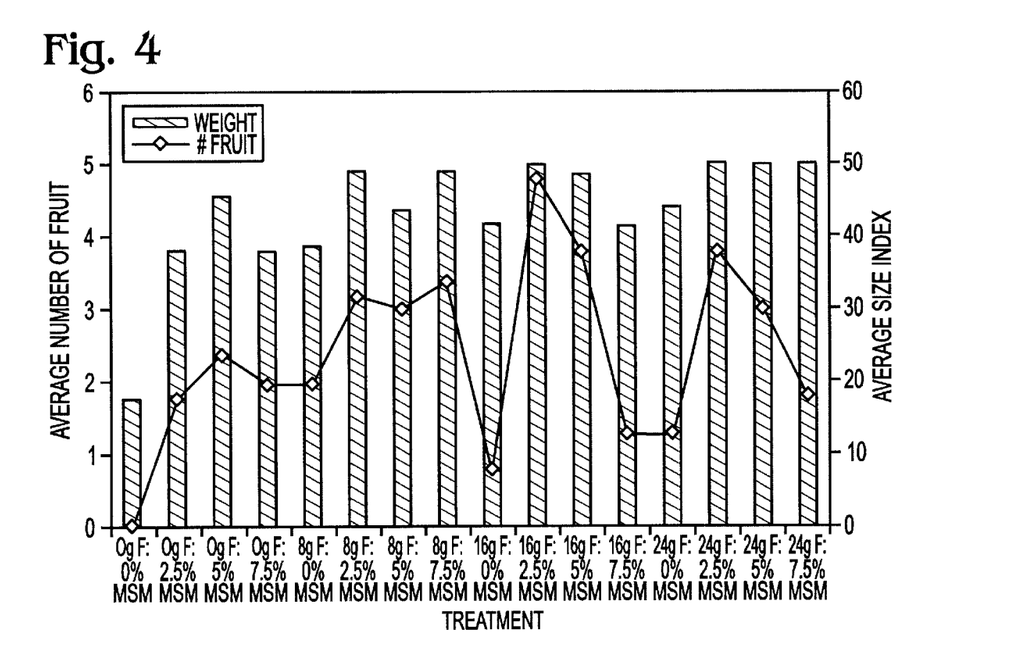
FIG. 4 is a diagram of growth characteristics for tomato grown with varying MSM and fertilizer rates.

Referring to FIGS. 1–2, two diagrams respectively shows the effects of meadowfoam seedmeal (MSM), commercial fertilizer (F) and various combinations of MSM+F on average fruit number and yield of two harvest of the same Jalapeno pepper plants. The second harvest coming approximately two months after the first. The average number of fruit and the average weight of that fruit are indicated. The data indicates that both the number of fruit and total yield are substantially improved with the incorporation of 2.5% and 5.0% MSM. While the incorporation of F provides substantially better results than no F, the benefit of additional quantities of F (over 8g) are less pronounced, and actually non-existent in treatment without MSM, see 16 g-no MSM and 32 g-no MSM compared to 8 g-no MSM. It should also be recognized that the combination of MSM+F produces better results than MSM alone, potentially suggesting that MSM facilitates uptake and/or utilization of F. The best results were at 2.5% MSM incorporation with 169 or 32 g of F. The reduced yields at 7.5% MSM are discussed below.

EXAMPLE II

Tomato Yield

Tomato plants (*Lycopersicon esculentumn* var. 'First Pick') were grown with the same experimental design discussed above for peppers. Referring to FIG. 2, a diagram shows the effects of meadowfoam seedmeal (MSM), commercial fertilizer (F) and various combinations of MSM+F on average fruit number and the average size of that fruit. The data indicates that total yield is substantially and consistently improved in each of the treatments that incorporate 2.5% MSM. This is also the case with 5% MSM incorporation.

EXAMPLE III

Potato Yield

Preliminary trials (above) showed MSM to have strong effects on potato growth and yield in greenhouse pots. Seed meal also has biocidal properties due to glucosinolate degradation compounds produced by seeds. Because of these results and certain implications about disease and insect control, trials were conducted to determine the potential value of MSM in potato production systems.

MSM was broadcast (i.e., spread) in bands approximately 34 inches wide over pre-marked 25-foot plot rows. Guard rows on either side were left untreated. Seed meal rates approximated 0%, 2%, 5% and 10% of a 6-inch furrow slice, volume/volume or 0, 31.4, 78.4 and 156.8 lbs./25 ft. plot, respectively. All plots were rototilled to incorporate the meal in the top 6 inches immediately after application. Russet Burbank seed pieces were then planted at standard spacings of 9.5 inches in 34-inch rows. Insecticides were omitted to better determine possible biocidal effects of the meadowfoam meal.

Incorporation of 2% (20+tons/acre) MSM strongly promoted Russet Burbank yield and quality. Application rates of approximately 10%, however, reduced marketable yields due in part to poor emergence but also delayed/reduced plant growth. The results at 5% incorporation were between the 2% and 10% results.

Compared to the untreated controls, 2% MSM increased both total and marketable yield and appeared to improve knobbiness and growth cracking, although the latter trends were not statistically significant. MDM at 2% did significantly reduce tuber hollow heart. Petiole nitrate analysis showed substantially higher nitrate levels for MSM treatments than for untreated controls. Untreated control plants were extremely deficient in nitrate despite the use of 1,000 lbs./acre of 15-15-15 fertilizer (N-P-K).

EXAMPLE IV

Tomato Growth

In addition to yield analysis, the above treatments of tomato were analyzed for growth characteristics. A size index related to the width and height of a fruit was created. Average number of fruit and average size index are indicated. Flowering was significantly and consistently increased in tomato plants treated with 2.5% and 5% MSM combined with F, but generally declined in tomato plants treated with 7.5% MSM. Root structures were significantly increased in tomato plants grown in MSM alone compared to F alone (data not shown).

EXAMPLES V–XVI

Mineral Nutrient Uptake

Figure 5:
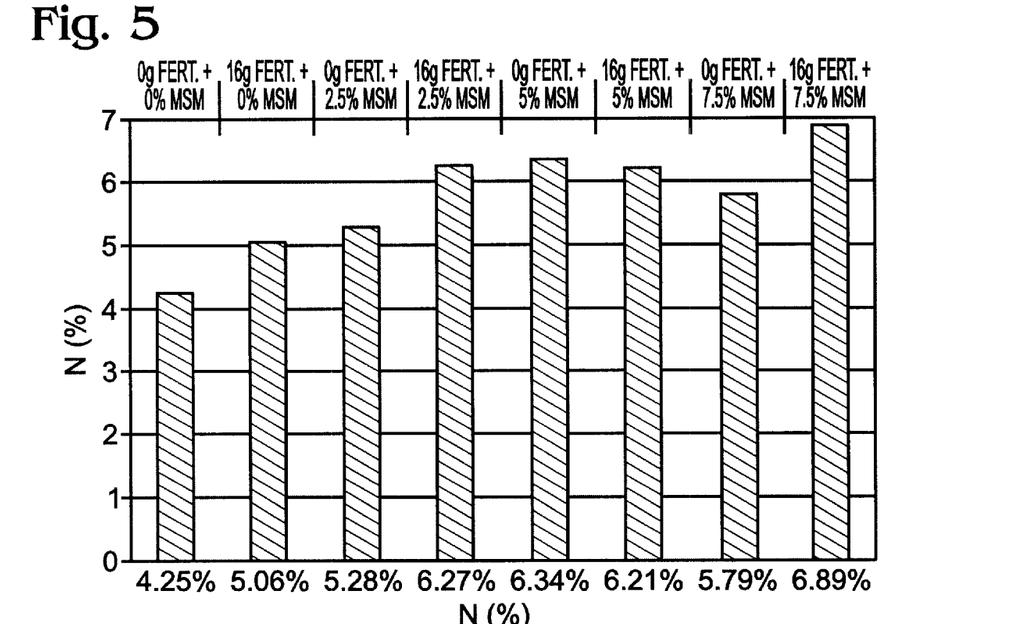
FIGS. 5–12 illustrate mineral nutrient uptake in pepper growth with varying MSM and fertilizer rates.
Figure 6:
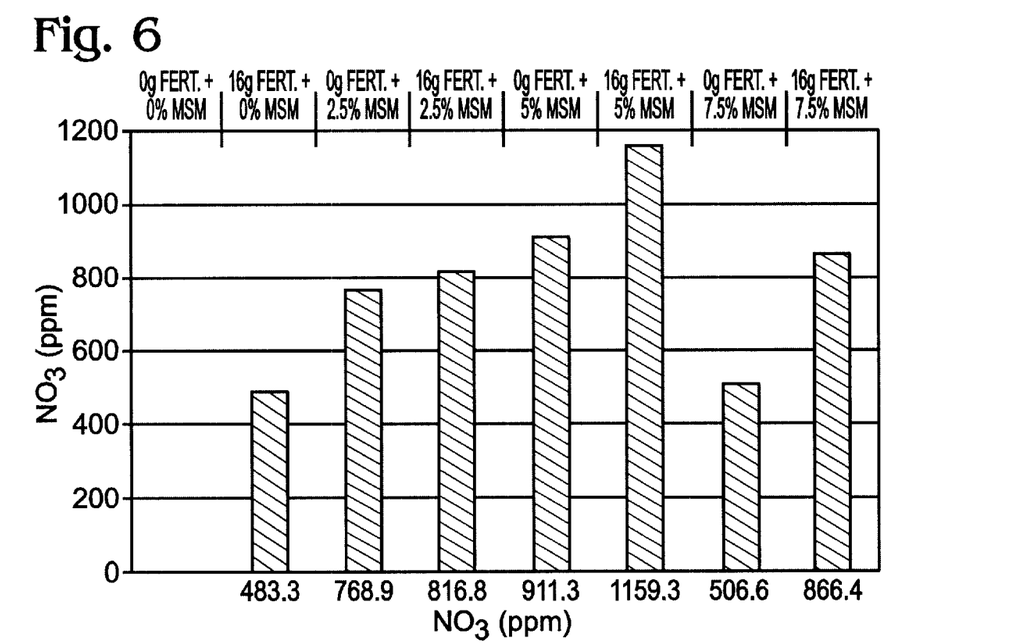
Figure 7:
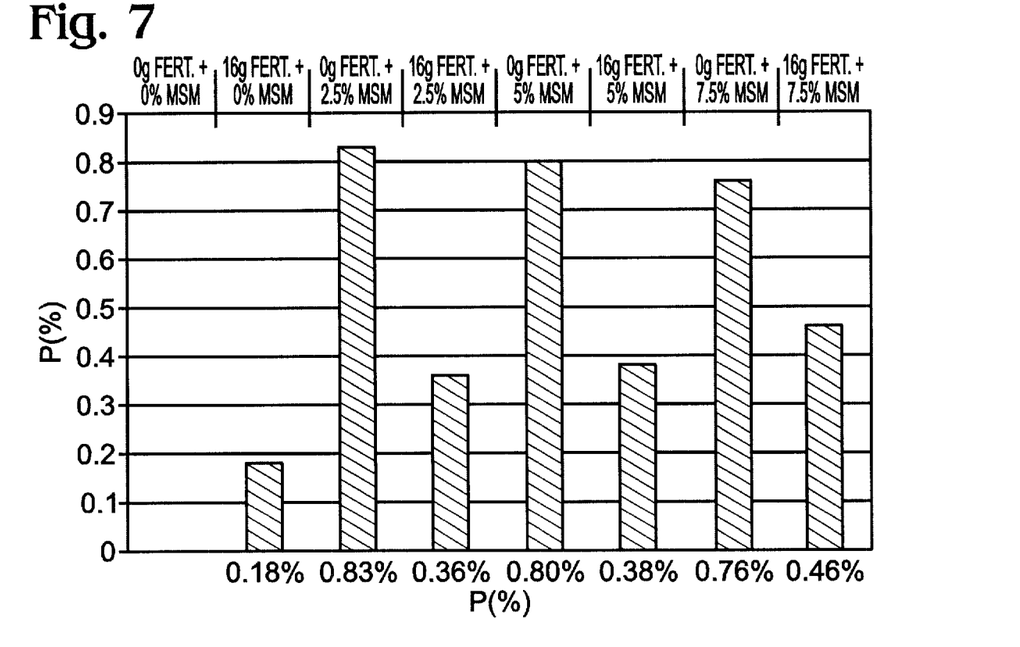
Figure 8:
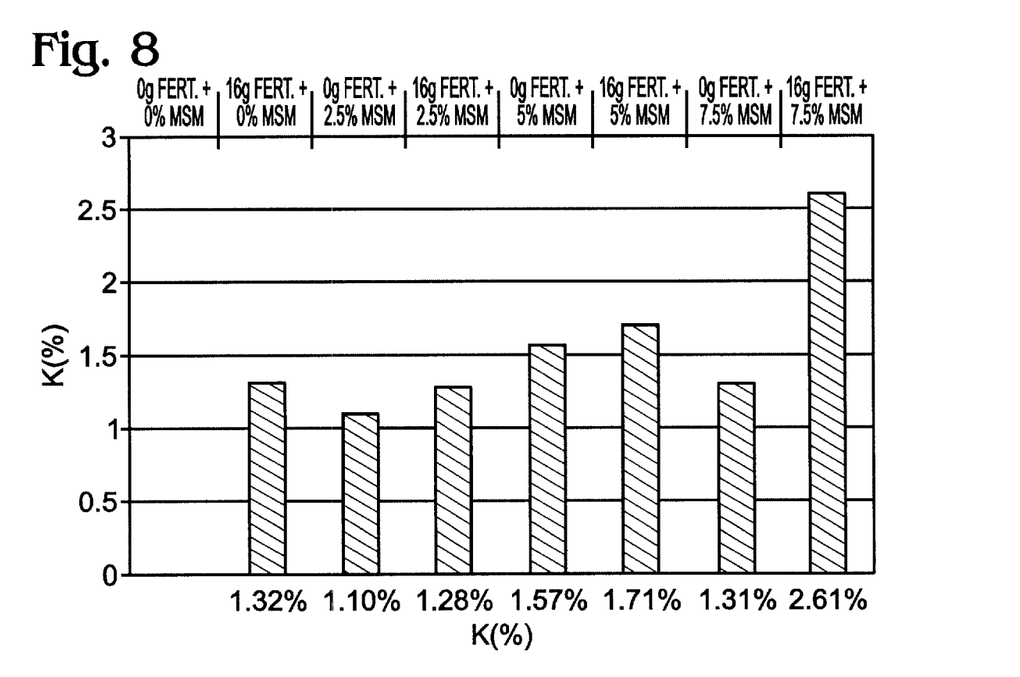
Figure 9:
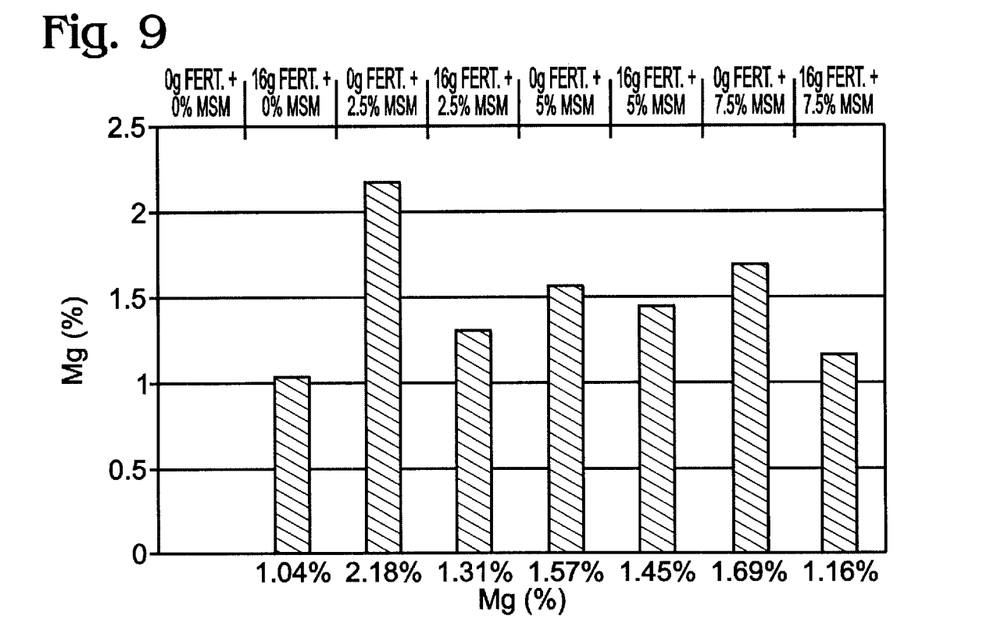
Figure 10:
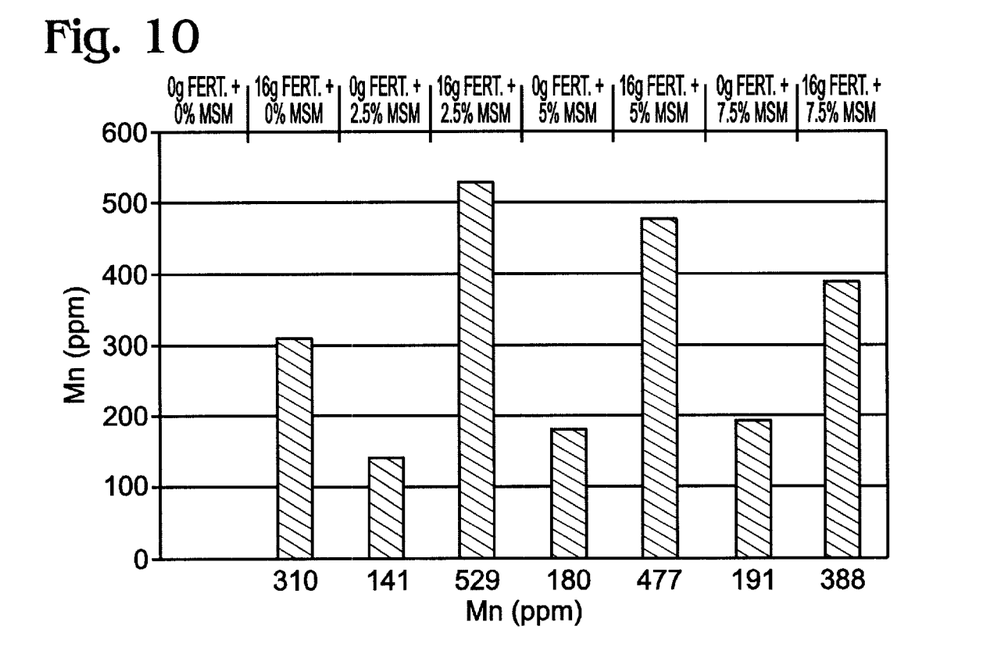
Figure 11:
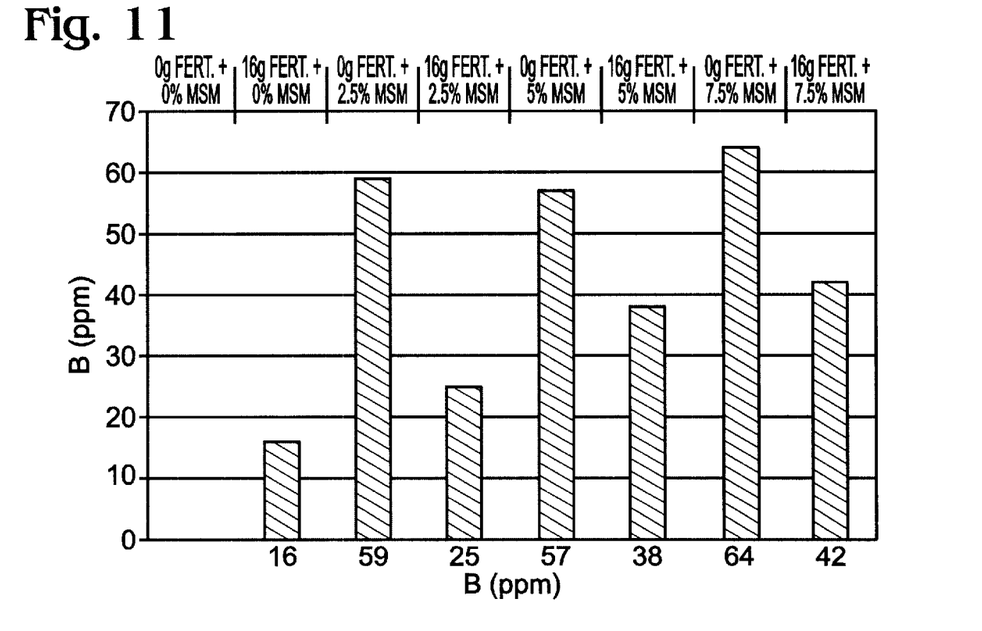
Figure 12:
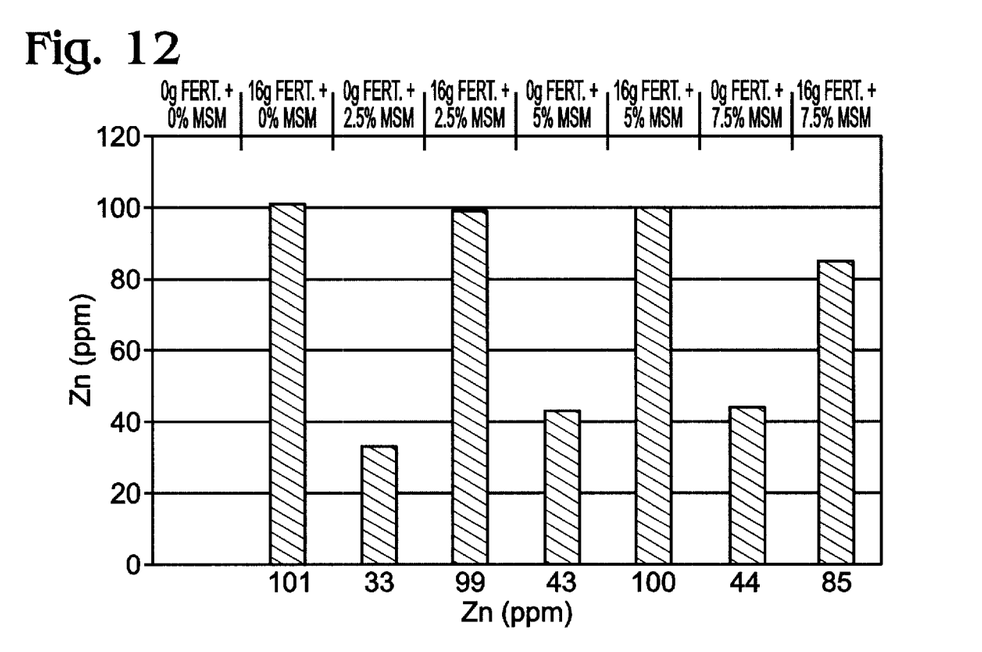

The mineral nutrient uptake measurements were taken from pepper plant leaves as discussed above in Example I—Pepper Yield. The results show significant differences in mineral nutrient for plants treated with fertilizer (F) alone, MSM alone or their combination. Total nitrogen (TN) concentrations in leaf tissues were not significantly different (FIG. 5), yet differences in nitrate ($NO^3$) concentrations (FIG. 6) were significant with 5% MSM only, and 5% MSM with 16 g F showing highest concentrations. Phosphorus concentrations (FIG. 7) show very significant contrasts between MSM and F treated plants with MSM alone showing significantly higher concentrations in all treatments. Potassium concentrations (FIG. 8) were not significant except for 7.5% MSM with F treated plants. Sulfur (S), calcium (Ca) and magnesium (Mg) concentrations (FIG. 9) were not significantly different except for significantly higher concentrations in plants treated with 2.5% MSM only compared to other treatments. Manganese (Mn) concentrations (FIG. 10) were significantly higher in all treatments of MSM with F compared to MSM only, with the greatest concentration in 2.5% MSM with F treated plants. Iron (Fe) concentrations were higher in plants treated with 5% and 7.5% MSM only compared to F only. Copper (Cu) concentrations are higher in F treated plants only compared to MSM only or in combination. Boron (B) concentrations (FIG. 11) were high in plants grown in MSM alone compared to treatments of F alone or in combinations with MSM, while Zinc (Zn) concentrations (FIG. 12) were higher in plants treated with F alone and F combined with MSM compared to plants treated with MSM alone.

In addition to the experiments carried out above, studies were also conducted to assess the effect of MSM on *Plasmodiophora brassicae* Wor. in Chinese mustard and cauliflower. Clubroot, a generic name describing the disease caused by *Plasmodiophora brassicae* Wor., a pathogenic fungi, has been a serious problem in cruciferous crops for over 250 years (Wellman, 1930). At present, this disease is widespread and occurs wherever cruciferous are cultivated. Breeding resistant crops is promising but not yet effective. Many soil sterilants and fungicides offer some control, but marginal values in the crops usually do not justify their use. Soil sterilants may also have malevolent environmental ramifications.

All treatments with meadowfoam plant residue incorporations (seedmeal and screenings) resulted in complete control of clubbing compared to controls. There was significant difference (p-value<0.01) in plant height between controls and treatments. Treatments with <5% MFM and 10% screenings resulted in significantly greater plant height compared to controls. A similar greenhouse trial was conducted that indicated control of clubroot at 4% (vol. by wt.) and significantly taller plants in treatments containing ≦4% (vol. by wt.) MSM.

Properties of MSM

Seeds of Limnanthes species are a known source of secondary metabolites like glucosinolates and phytoecdysteroids, which have allelochemical activity and are generally recognized as plant defense mechanisms against predation and disease (Brown and Morra, 1997; Delaquis and Mazza, 1995; Gamliel and Stapleton, 1993; Brown et al., 1991; Bartelt and Mikolajczak, 1989). A large body of evidence exists regarding the toxicological effects and properties of glucosinolate aglycones, which are found in many cultivated human foods, fish and animal fodders (Brown and Morra, 1997; Rosa et al., 1997; Fenwick et al., 1991, 1989, 1983; Mithen et al., 1987). It is suspected that these and like compounds are responsible for the phytotoxic affects of MSM when applied at higher rates.

The natural precursors of glucosinolates are amino acids, based on similarities between the chemical structures of glucosinolates and amino acids (Verkerk, et al. 1998; Rosa, et al. 1997; Kjaer and Conti 1954). The biosynthesis of glucosinolate glucolimnanthin (the major glucosinolate in MSM) starts with modification of the amino acids phenylalanine and/or tyrosine (or chain-extended derivatives of this class) via an aldoxime intermediate. The same amino acid precursors and modifications take place in the biosynthetic route of various plant hormones like auxin and salicylic acid. The biosynthetic pathways in some species of Limnanthes may thus provide precursors of novel hormone like substances (HLS) that accumulate in seed tissues and are present in seedmeal for enhancing growth.

There is no evidence from prior studies using seedmeals that show significant growth stimulus similar to the effects of plants amended with MSM as discussed herein. It thus appears that MSM contains novel HLS that are exogenously available and subsequently utilized by recipient plants and/or elicit hormonal activity through physiological processes within recipient plants that result in stimulated growth responses. Based upon specific plant growth response in our studies, it is speculated that MSM contains novel HLS that cause effects similar to those of the plant hormone auxin. In fact, the unidentified HLS may be a unique auxin or mixture of auxin precursors that can be utilized by other plant species.

It should be recognized that some synthetic pesticides (i.e. 2,4-D) applied at very low rates show hormonal activity (i.e., cell elongation, etc.) in some plants but result in phytotoxicity at suggested rates of application. Similarly, plants grown in media amended with 2.5–5% MSM (v/v), show significant growth and yields, but at rates >7.5% MSM show reduced growth and in some instances phytotoxicity in some plants.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A planting medium composition comprising by volume an amount of meadowfoam seedmeal that is in the range of greater than 0% to approximately 7%.

2. The composition of claim 1, comprising about 1–6% meadowfoam seedmeal by volume.

3. The composition of claim 1, comprising about 2–6% meadowfoam seedmeal by volume.

4. The composition of claim 1, comprising about 2–5% meadowfoam seedmeal by volume.

5. The composition of claim 1, further comprising supplemental fertilizer in a form that can be readily absorbed by a plant grown in the composition.

6. The composition of claim 5, wherein said fertilizer includes at least one of nitrogen, potassium and phosphorous.

7. The composition of claim 6, wherein said fertilizer includes nitrogen, potassium and phosphorous.

8. The composition of claim 1, wherein said meadowfoam seedmeal includes seedmeal from *Limnanthes alba* Hartweg ex. Benth.

9. A method of forming a plant growth medium, including the step of combining meadowfoam seedmeal with plant growth medium material to achieve a plant growth medium that has approximately 7% or less, though greater than 0%, meadowfoam seedmeal by volume.

10. The method of claim 9, wherein said combining step achieves a plant growth medium that has approximately 1–6% meadowfoam seedmeal by volume.

11. The method of claim 9, wherein said combining step achieves a plant growth medium that has approximately 2–5% meadowfoam seedmeal by volume.

12. The method of claim 9, further comprising the step of combining fertilizer with said plant growth medium in a form that can be readily absorbed by a plant grown in the medium, said fertilizer including at least one of supplemental nitrogen, phosphorous and potassium.

13. The method of claim 9, wherein said meadowfoam seedmeal includes seedmeal from the variety *Limnanthes alba* Hartweg ex. Benth.

14. The method of claim 9, wherein said combining step includes at least one of the steps of:

top-dressing; or mixing;

said meadowfoam seedmeal with the plant growth medium material.

15. The method of claim 9, wherein said combining step includes the steps of spreading meadowfoam seedmeal over a plant growth medium and tilling to mix the meadowfoam seedmeal with the plant growth medium.

16. The method of claim 9, wherein said combining step includes the step of spreading meadowfoam seedmeal over a plant growth medium at a rate of about 20 tons or less per acres.

17. A planting medium composition comprising by volume about 7% or less, though greater than 0%, meadowfoam seedmeal that includes seedmeal from *Limnanthes alba* Hartweg ex. Benth.

18. The planting medium composition of claim 17, comprising about 1–6% meadowfoam seedmeal by volume.

19. The planting medium composition of claim 18, further comprising supplemental fertilizer including at least one of nitrogen, phosphorous and potassium.

* * * * *